(12) United States Patent
Sagawa

(10) Patent No.: US 12,415,346 B2
(45) Date of Patent: Sep. 16, 2025

(54) DECORATIVE SHEET AND METHOD FOR PRODUCING THE SAME

(71) Applicant: TOPPAN INC., Tokyo (JP)

(72) Inventor: Koichi Sagawa, Tokyo (JP)

(73) Assignee: TOPPAN INC., Tokyo (JP)

( * ) Notice: Subject to any disclaimer, the term of this patent is extended or adjusted under 35 U.S.C. 154(b) by 105 days.

(21) Appl. No.: 18/126,899

(22) Filed: Mar. 27, 2023

(65) Prior Publication Data

US 2023/0256470 A1 Aug. 17, 2023

Related U.S. Application Data

(63) Continuation of application No. PCT/JP2020/042094, filed on Nov. 11, 2020.

(30) Foreign Application Priority Data

Sep. 28, 2020 (JP) .................................. 2020-162648

(51) Int. Cl.
| | | |
|---|---|---|
| *B05D 7/00* | (2006.01) | |
| *B32B 27/30* | (2006.01) | |
| *B05D 5/06* | (2006.01) | |

(52) U.S. Cl.
CPC .............. *B32B 27/304* (2013.01); *B05D 7/57* (2013.01); *B05D 5/06* (2013.01); *B05D 2201/00* (2013.01);
(Continued)

(58) Field of Classification Search
CPC ............................ B32B 2451/00; B32B 27/16
See application file for complete search history.

(56) References Cited

U.S. PATENT DOCUMENTS

2019/0110478 A1* 4/2019 Isobe ..................... A01N 25/10

FOREIGN PATENT DOCUMENTS

| JP | H10-245495 A | 9/1998 |
|---|---|---|
| JP | H11-139094 A | 5/1999 |

(Continued)

OTHER PUBLICATIONS

English language translation of JP H11139094A, generated on Oct. 23, 2024 with Espacenet website (https://worldwide.espacenet.com).*

(Continued)

*Primary Examiner* — Humera N. Sheikh
*Assistant Examiner* — Julia L Rummel
(74) *Attorney, Agent, or Firm* — Foley & Lardner LLP

(57) ABSTRACT

Decorative sheets used for decorative materials, such as for general fittings, and methods for producing, and prevents discoloration due to contact between chlorine and silver, including at least a polyvinyl chloride resin layer, a pattern layer, and a surface protective layer, the surface protective layer contains silver components including silver and is free from chlorine-containing components. The surface protective layer may be composed of a plurality of laminated layers that include at least one layer containing the silver components; the laminated layers of the surface protective layer may include at least one layer disposed adjacent to the polyvinyl chloride resin layer and being free from silver components; the silver components may each be supported on an inorganic substance; the surface protective layer may have a cross-linked structure; and the cross-linked structure of the surface protective layer may be formed by use of ultraviolet light or an electron beam.

14 Claims, 1 Drawing Sheet

(52) U.S. Cl.
CPC ........ *B05D 2506/25* (2013.01); *B32B 27/308* (2013.01); *B32B 2255/10* (2013.01); *B32B 2255/28* (2013.01); *B32B 2451/00* (2013.01)

(56) References Cited

FOREIGN PATENT DOCUMENTS

| JP | H11-277685 A | 10/1999 |
|----|--------------|---------|
| JP | 2014-065283 A | 4/2014 |
| JP | 2020-040267 A | 3/2020 |

OTHER PUBLICATIONS

English language translation of JP H11277685A, generated on Oct. 23, 2024 with Espacenet website (https://worldwide.espacenet.com).*

International Searching Authority, "International Search Report," issued in connection with International Patent Application No. PCT/JP2020/042094, Jan. 26, 2021.

International Searching Authority, "Written Opinion," issued in connection with International Patent Application No. PCT/JP2020/042094, Jan. 26, 2021.

Japanese Patent Office, "Notification of Reasons for Rejection," issued in connection with Japanese Patent Application No. 2020-162648, dated Mar. 2, 2021.

* cited by examiner

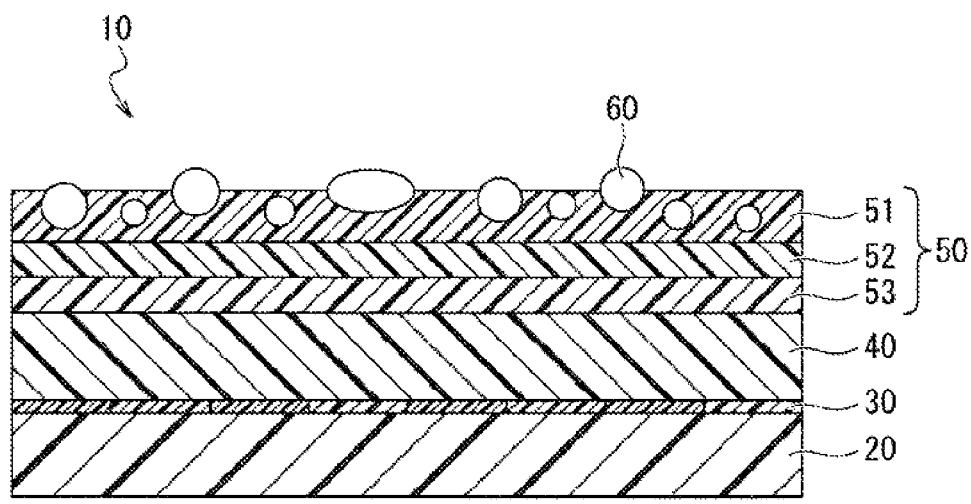

DECORATIVE SHEET AND METHOD FOR PRODUCING THE SAME

CROSS-REFERENCE TO RELATED PATENT APPLICATIONS

Japan Priority Application 2020-162648, filed Sep. 28, 2020 including the specification, drawings, claims and abstract, is incorporated herein by reference in its entirety. This application is a Continuation of US Application PCT/JP2020/042094, filed Nov. 11, 2020, incorporated herein by reference in its entirety.

TECHNICAL FIELD

The present invention relates to decorative sheets used, for example, for decorative materials, such as for general fittings, and methods for producing the same.

BACKGROUND ART

Although silver-based inorganic antimicrobial and antiviral agents composed of inorganic materials with silver ions supported thereon are characterized by having a high degree of safety, maintaining their antimicrobial properties over a long period of time, and exhibiting high heat resistance compared to organic antimicrobial agents, it has been pointed out that they easily undergo discoloration (see paragraph [0002] of PTL 1).

CITATION LIST

Patent Literature

[PTL 1] JP H10-245495 A

SUMMARY OF THE INVENTION

Technical Problem

Pronounced discoloration is known to occur particularly when the above silver-based inorganic antimicrobial and antiviral agents are used in combination with chlorine-containing materials.

There are various discoloration mechanisms, but it is known that white silver chloride is produced by the reaction of silver ions and chloride ions when the above silver-based inorganic antimicrobial and antiviral agents are used in combination with chlorine-based materials.

Decorative sheets used for surface decoration on building materials may be comprised of polyvinyl chloride, polyethylene terephthalate, polyolefin, paper, or a combination thereof; for uses that require nonflammability, a high degree of post-processing suitability, or the like, decorative sheets comprised of polyvinyl chloride are employed.

Unfortunately, if decorative sheets comprised of polyvinyl chloride are formed that contain silver-based additive particles for imparting antimicrobial and antiviral properties to the decorative sheets, problems such as discoloration may occur, which is a technical problem.

The present invention has been contemplated to solve the above problem; an object of the present invention is to provide antimicrobial and antiviral decorative sheets comprised of polyvinyl chloride.

Solution to Problem

A decorative sheet according to an aspect of the present invention comprises:
a polyvinyl chloride resin layer;
a pattern layer; and
a surface protective layer, wherein
the surface protective layer contains silver components including silver and is free from chlorine-containing components.

The decorative sheet according to another aspect of the present invention is characterized in that:
the surface protective layer comprises a plurality of laminated layers; and
the laminated layers of the surface protective layer include at least one layer containing the silver components.

The decorative sheet according to another aspect of the present invention is characterized in that:
the laminated layers of the surface protective layer include at least one layer disposed adjacent to the polyvinyl chloride resin layer and being free from the silver components.

The decorative sheet according to another aspect of the present invention is characterized in that:
the surface protective layer contains inorganic substances; and
each of the inorganic substances has one or more of the silver components supported thereon.

The decorative sheet according to another aspect of the present invention is characterized in that:
the surface protective layer has a cross-linked structure.

The decorative sheet according to another aspect of the present invention is characterized in that:
the cross-linked structure of the surface protective layer is formed by use of ultraviolet light.

The decorative sheet according to another aspect of the present invention is characterized in that:
the cross-linked structure of the surface protective layer is formed by use of an electron beam.

The decorative sheet according to another aspect of the present invention is characterized in that:
the surface protective layer comprises an outermost layer;
the outermost layer contains silver-based additive particles each including a respective one of the inorganic substances; and
the following expression (1) is satisfied:

$$D50 \leq D\text{surf} < 3 \times D50 \tag{1}$$

where:
$D50$ is a median diameter (μm) of the silver-based additive particles; and
$D\text{surf}$ is a coating amount (g/m$^2$) defined as a density of the outermost layer per square meter thereof.

The decorative sheet according to another aspect of the present invention is characterized in that:
the surface protective layer comprises an outermost layer;
the outermost layer contains silver-based additive particles as silver-based additive components; and
the following expression (2) is satisfied:

$$A \times B \times C \geq 10 \tag{2}$$

where:
$A$ is a solid-content concentration (mass %) of the silver-based additive components in the outermost layer;
$B$ is a proportion (mass %) of silver in the silver-based additive particles; and
$C$ is a density (g) of the silver-based additive particles per square meter of the outermost layer.

A method according to another aspect of the present invention for producing a decorative sheet, including:
  laminating a pattern layer on a surface of a printing substrate;
  laminating transparent polyvinyl chloride on a surface of the pattern layer to form a transparent polyvinyl chloride resin layer thereon; and
  laminating a transparent surface protective layer on a surface of the polyvinyl chloride resin layer, the surface protective layer being composed of an undercoat layer and a top coat layer,
  the step of laminating the transparent surface protective layer including:
  a first step of applying, to the surface of the polyvinyl chloride resin layer, a first coat of resin free from silver components including silver, and curing the first coat to form the undercoat layer; and
  a second step of applying, to a surface of the undercoat layer, a top coat of resin containing the silver components while being free from chlorine-containing components, and then curing the top coat to cause cross-linking thereof, to thereby form the top coat layer.

Advantageous Effects of Invention

The above aspects of the present invention prevent discoloration due to contact between chlorine and silver.

BRIEF DESCRIPTION OF THE DRAWINGS

The FIGURE is a cross-sectional view of a decorative sheet according to a first embodiment.

DETAILED DESCRIPTION

Embodiments of the present invention will be described below with reference to the drawings. In the following description of the drawings to be referred, components or functions identical with or similar to each other are given the same or similar reference signs, unless there is a reason not to. It should be noted that the drawings are only schematically illustrated, and thus the relationship between thickness and two-dimensional size of the components, and the thickness ratio between the layers, are not to scale. Therefore, specific thicknesses and dimensions should be understood in view of the following description. As a matter of course, dimensional relationships or ratios may be different between the drawings.

Further, the embodiments described below are merely examples of configurations for embodying the technical idea of the present invention. The technical idea of the present invention does not limit the materials, shapes, structures, arrangements, and the like of the components to those described below. The technical idea of the present invention can be modified variously within the technical scope defined by the claims. The present invention is not limited to the following embodiments within the scope not departing from the spirit of the present invention. For the sake of clarity, the drawings may be illustrated in an exaggerated manner as appropriate.

In any group of successive numerical value ranges described in the present specification, the upper limit value or lower limit value of one numerical value range may be replaced with the upper limit value or lower limit value of another numerical value range. In the numerical value ranges described in the present specification, the upper limit values or lower limit values of the numerical value ranges may be replaced with values shown in examples. The configuration according to a certain embodiment may be applied to other embodiments.

The embodiments of the present invention are a group of embodiments based on a single unique invention. The aspects of the present invention are those of the group of embodiments based on a single invention. Configurations of the present invention can have aspects of the present disclosure. Features of the present invention can be combined to form the configurations. Therefore, the features of the present invention, the configurations of the present invention, the aspects of the present disclosure, and the embodiments of the present invention can be combined, and the combinations can have a synergistic function and exhibit a synergistic effect.

First Embodiment

A first embodiment of the present invention will be described below with reference to the drawing.

Here, the drawing is schematic, and the relationship between the thickness and the horizontal dimensions, the ratio between the thicknesses of respective layers, and the like are not to scale. Further, the embodiment described below merely presents an example configuration for embodying the technical idea of the present invention, and the technical idea of the present invention does not limit the materials, shapes, structures, and the like of the components to those described below. The technical idea of the present invention can be variously modified within the technical scope defined in the claims.

[Decorative Sheet 10]

In the FIGURE, the reference number 10 represents a decorative sheet. The decorative sheet 10 may be used, for example, for decorative materials, such as for general fittings.

The decorative sheet 10 is composed of the following layers laminated in sequence.

Each of these layers will be described later.
  (1) Printing substrate 20
  (2) Pattern layer 30
  (3) Polyvinyl chloride resin layer 40
  (4) Surface protective layer 50

The decorative sheet 10 is not limited to the above layers (1) to (4). Although not illustrated, the surface of the surface protective layer 50, for example, may have an uneven shape formed such as by embossing so as to match the pattern layer 30.

[Printing Substrate 20]

The printing substrate 20 serves as a support member of the decorative sheet 10 of the present invention; specifically, the printing substrate 20 may be, for example, a colored sheet comprised of polyvinyl chloride, and have a thickness of, for example, 70 μm.

Although a colored sheet comprised of polyvinyl chloride is presented above as an example of the printing substrate 20, this is not intended to be limiting, and paper may be used instead. Further, although 70 μm is presented above as an example of the thickness of the colored sheet, this is not intended to be limiting.

[Pattern Layer 30]

The pattern layer 30 is formed on the surface of the printing substrate 20 using a printing method. The pattern layer 30 is provided to impart designability to a target decorative sheet 10.

Examples of the printing method include gravure printing, offset printing, relief printing, flexographic printing, screen printing, inkjet printing, electrostatic printing, and the like. The printing method is not limited to the above example methods, and may be any conventionally known image forming means, such as a hand drawing method, a marbling method, a transfer method, a photographic method, an electrophotographic method, a photosensitive resin method, a vacuum deposition method, a chemical corrosion method, a thermosensitive coloring method, or a discharge breakdown method.

The pattern layer 30 has any type of pattern according to the intended use, user's taste, or the like; typical patterns thereof include, for example, a wood grain pattern, a stone pattern, an abstract pattern, and the like. The type of pattern is not limited to the above examples, and may be, for example, solid printing on the entire surface.

Printing ink used for the printing method may be, for example, vinyl chloride-vinyl acetate copolymer-based ink (cyan, magenta, yellow).

Although vinyl chloride-vinyl acetate copolymer-based ink is presented above as an example of the printing ink, this is not intended to be limiting; for example, the printing ink may be made by dispersing, in a binder composed of synthetic resin or the like, a colorant, such as an organic or inorganic dye or pigment, together with a solvent or a diluent, and appropriate additives, such as an extender pigment, a filler, a tackifier, a plasticizer, a stabilizer, a dispersant, an antifoaming agent, a leveling agent, a surfactant, and a drying agent.

[Polyvinyl Chloride Resin Layer 40]

The polyvinyl chloride resin layer 40 is laminated on the surface of the pattern layer 30 and transparent; thus, the pattern layer 30 can be seen from the surface of the polyvinyl chloride resin layer 40.

Specifically, the polyvinyl chloride resin layer 40 is formed by laminating transparent polyvinyl chloride using a thermal lamination method. The thickness of the transparent polyvinyl chloride is set to, but is not limited to, for example, 100 µm.

[Surface Protective Layer 50]

The surface protective layer 50 is provided to impart surface physical properties, such as abrasion resistance and water resistance, to the surface of the decorative sheet 10.

Further, the surface protective layer 50 contains silver-based additive particles 60 each comprising a silver component including silver, thus imparting antiviral properties.

The surface protective layer 50 does not contain any chlorine-containing component. This configuration is employed to prevent discoloration due to contact between silver components of the silver-based additive particles 60 and chlorine.

[Multilayered Surface Protective Layer 50]

The surface protective layer 50 is formed by gravure coating to have a plurality of layers, for example first to third surface protective layers 51 to 53 comprised of an acrylic material.

Note that, although a three-layer configuration is presented above as an example configuration of the surface protective layer 50, this is not intended to be limiting; the surface protective layer 50 may have any number of layers as long as it is a multilayered layer, for example two layers or four or more layers (not shown).

At least one layer selected from the first to third surface protective layers 51 to 53, for example only the first surface protective layer 51, disposed as the outermost layer, contains silver-based additive particles 60 each comprising a silver component including silver.

Note that, although the first surface protective layer 51 is presented above as an example of the at least one layer, this is not intended to be limiting; although not shown, the second surface protective layer 52, disposed as an intermediate layer, may be added to the at least one layer.

Among the first to third surface protective layers 51 to 53, at least one layer adjacent to the polyvinyl chloride resin layer 40, for example the third surface protective layer 53, is free from silver-based additive particles 60 each comprising a silver component including silver.

Note that, although the third surface protective layer 53 is presented above as an example of the at least one layer adjacent to the polyvinyl chloride resin layer 40, this is not intended to be limiting; although not shown, the second surface protective layer 52, disposed as an intermediate layer, may be added to this at least one layer.

With only at least one of layers of the multilayered surface protective layer 50 containing silver components and at least one of the layers of the multilayered surface protective layer 50 adjacent to the polyvinyl chloride resin layer 40 not containing silver components, as described above, contact between chlorine and silver is prevented at an interface between laminated layers; thus, the cause of discoloration is completely avoided.

[First to Third Surface Protective Layers 51 to 53]

The first surface protective layer 51 is disposed as the outermost layer; the third surface protective layer 53 is disposed next to the polyvinyl chloride resin layer 40; and the second surface protective layer 52 is disposed between the first surface protective layer 51 and the third surface protective layer 53.

The first surface protective layer 51 contains silver-based additive particles 60, thus imparting antiviral properties.

The second surface protective layer 52 and the third surface protective layer 53 may or may not contain silver-based additive particles 60.

For example, in the case of the second surface protective layer 52 and the third surface protective layer 53 being designed to contain no silver-based additive particles 60, the third surface protective layer 53 is free from the effects of discoloration due to contact between silver components of silver-based additive particles 60 and chlorine, which provides a higher degree of freedom in selecting the material of the third surface protective layer 53. In this case, the material of the third surface protective layer 53 is not limited to an acrylic material, and may be, for example, a vinyl chloride-vinyl acetate copolymer including a chlorine-containing component.

[Silver-Based Additive Particles 60]

The silver-based additive particles 60 each contain a silver component including silver, thus imparting antiviral properties.

The silver component is supported on an inorganic substance.

Here, the inorganic material is, but is not limited to, glass.

With silver being supported on an inorganic substance, loss of a silver component over time and migration of a silver component to the polyvinyl chloride resin layer are prevented.

[Cross-Linked Structure]

The surface protective layer 50 has a cross-linked structure.

Cross-linking of the surface protective layer 50 enables blocking of the migration of a silver component to the polyvinyl chloride resin layer.

The cross-linked structure is formed by applying high energy such as ultraviolet light or an electron beam to the surface protective layer 50 to cause cross-linking thereof, resulting in a higher degree of cross-linking, which further suppresses the migration of silver to the polyvinyl chloride resin layer.

For example, ionizing radiation-curable resins can be used. Such an ionizing radiation-curable resin may be, but is not limited to, a transparent resin containing, as a main component, a prepolymer (including oligomer) and/or monomer having, in a molecule, a radical polymerizable double bond, which is polymerizable and crosslinkable by irradiation with ionizing radiation such as UV light, an electron beam, or the like. The above prepolymer or monomer may be used singly or in a combination of two or more. The curing reaction is typically a crosslinking curing reaction.

[Relationship Between Median Diameter of Silver-Based Additive Particles 60 and Coating Amount]

The following expression (1) holds:

$$D50 \leq Dsurf < 3 \times D50 \quad (1)$$

where D50 is the median diameter (μm) of silver-based additive particles 60 each comprising an inorganic substance and silver supported on the inorganic substance, that is, a mixture of silver and an inorganic substance; and Dsurf is a coating amount ($g/m^2$) defined as the density of the outermost layer of the surface protective layer 50 per square meter.

Here, the term "median diameter" refers to a median diameter of a mixture of silver and inorganic substances. That is, the above expression (1) represents the relationship between the value of D50 (μm) and the value of Dsurf ($g/m^2$).

With the above expression (1) holding, parts of silver-supporting carriers protrude from the surface protective layer 50, which enhances antimicrobial and antiviral effects.

[Relationship Between Solid-Content Concentration of Silver-Based Additive Component, Proportion of Silver, and Density]

The following expression (2) holds:

$$A \times B \times C \geq 10 \quad (2)$$

where A is the solid-content concentration (mass %) of the silver-based additive components in the outermost layer of the surface protective layer 50; B is the proportion (mass %) of silver in the silver-based additive particles 60; and C is the density (g) of the silver-based additive particles 60 per square meter of the outermost layer of the surface protective layer 50.

Here, the term "silver-based additive components" refers to silver components and inorganic carriers (silver components+inorganic carriers). That is, the above expression (2) means that A is the concentration (%) of silver-based additive particles; B is the concentration (%) of silver (active ingredient) in the silver-based additive particles; C is the above density of the silver-based additive particles (the quantity of silver per unit area) the basis weight of the outermost layer of the surface protective layer 50; and sufficient antiviral properties are exhibited only if the result of A×B×C is a predetermined value (10 or more in the present invention).

With the above expression (2) holding, the product of the component amount of the silver-based additive particles 60, the amount of silver in the silver-based additive particles 60, and the above density corresponds to the concentration of the active ingredient, and if this product is 10 or more, an antiviral activity value of 3 or more (reduction of viruses by 99.9%) is achieved.

[Production Method]

A method for producing the decorative sheet 10 having the above-described configuration is as follows.

Using a 70-μm-thick colored sheet (comprised of polyvinyl chloride) as a printing substrate 20, vinyl chloride-vinyl acetate copolymer-based ink (cyan, magenta, yellow) is gravure printed on the surface of the printing substrate 20 to form a pattern layer 30.

Transparent polyvinyl chloride is laminated at a thickness of 100 μm on the surface of the pattern layer 30 using a thermal lamination method to form a polyvinyl chloride resin layer 40.

A surface protective layer 50 having three layers comprised of an acrylic material is formed by gravure coating on the surface of the polyvinyl chloride resin layer 40 to thereby produce a decorative sheet 10.

The surface protective layer 50 has three layers, namely the first to three surface protective layers 51 to 53; they are broadly divided into "undercoat" (e.g., the third surface protective layer 53, which is hereinafter also referred to as "undercoat" or "undercoat layer") and "top coat" (e.g., the first surface protective layer 51, which is hereinafter also referred to as "top coat" or "top layer").

The second surface protective layer 52 is configured as the undercoat layer or the top coat layer.

Specifically, the surface protective layer 50 is composed of the undercoat layer (e.g., the third surface protective layer 53) and the top coat layer (e.g., the first surface protective layer 51).

The surface protective layer 50 is formed using a method including the following steps:

(1) First Step

The first step is a step of applying, to the surface of the polyvinyl chloride resin layer 40, a first coat of resin free from silver components including silver (e.g., silver-based additive particles 60), and curing the first coat to form an undercoat layer (e.g., the third surface protective layer 53).

(2) Second Step

The second step is a step of applying, to the surface of the undercoat layer (e.g., the third surface protective layer 53), a top coat of resin containing silver components (e.g., silver-based additive particles 60) while being free from chlorine-containing components, and then curing the top coat to cause cross-linking thereof, to form a top coat layer (e.g., the first surface protective layer 51).

[Undercoat Layer]

As the base material of the undercoat layer (e.g., the third surface protective layer 53) or undercoat, one of the following products is used:

(1) Coating material product: UC Clear, curing agent W325N=100/10, thermosetting resin, available from DIC Graphics Corporation (hereinafter also referred to as "UC Clear")

Material: acrylic+isocyanate (2) Coating material product: UVT Clear, UV-curable resin, available from DIC Graphics Corporation (hereinafter also referred to as "UVT Clear")

Material: acrylic (3) Coating material product: EBT Clear, EB-curable resin, available from DIC Graphics Corporation (hereinafter also referred to as "EBT Clear")

Material: acrylic

For the undercoat, silver-based additive particles 60 (hereinafter also referred to as "antiviral agent"), for example, are not used. Note that silver-based additive particles 60 (antiviral agent) may be used for the undercoat.

[Top Coat Layer]

The base material of the top coat layer (e.g., the first surface protective layer 51) or top coat is the same as that of the undercoat.

As silver-based antiviral additive particles 60 (antiviral agent) for the top coat, one of the following products is used.

(1) Antiviral agent product: PTC-NT ANV additive (ST), available from Dainichiseika Color & Chemicals Mfg. Co., Ltd., amount of silver supported=3%, median diameter (D50) of 3 μm (hereinafter also referred to as "PTC-NT ANV additive (ST)")

The amount of the PTC-NT ANV additive (ST) contained (on a dry basis) may be set to, for example, 1 wt % to 5 wt %.

The density of the PTC-NT ANV additive (ST) is set to 1 g/m² to 3 g/m².

(2) Antiviral agent product: PTC-NT ANV additive (S1), available from Dainichiseika Color & Chemicals Mfg. Co., Ltd., amount of silver supported=2%, median diameter (D50) of 1 µm (hereinafter also referred to as "PTC-NT ANV additive (S1)")

The amount of the PTC-NT ANV additive (S1) contained (on a dry basis) is set to be the same as that of the PTC-NT ANV additive (ST).

The density of the PTC-NT ANV additive (S1) is set to be the same as that of the PTC-NT ANV additive (ST).

(3) Antiviral agent product: BIOSAIDO TB-B100, available from Taisho Technos Co., Ltd., amount of silver supported=1%, median diameter (D50) of 5 µm (hereinafter also referred to as "BIOSAIDO TB-B100")

The amount of the BIOSAIDO TB-B100 contained (on a dry basis) may be set to, for example, 5 wt %.

The density of the BIOSAIDO TB-B100 is set to be the same as that of the PTC-NT ANV additive (ST).

Advantageous Effects of Embodiment

Advantageous effects of the present embodiment are as follows:

(1) According to the present embodiment, in the decorative sheet 10 including at least the polyvinyl chloride resin layer 40, pattern layer 30, and surface protective layer 50, the surface protective layer 50 contains silver components including silver (e.g., silver-based additive particles 60) and is free from chlorine-containing components. This configuration prevents discoloration due to contact between chlorine and silver.

(2) According to the present embodiment, the surface protective layer 50 is composed of a plurality of layers; the layers of the surface protective layer 50 include at least one layer containing silver components (e.g., silver-based additive particles 60); and the layers of the surface protective layer 50 include at least one other layer disposed adjacent to the polyvinyl chloride resin layer 40 and not containing silver components (e.g., silver-based additive particles 60). This configuration prevents contact between chlorine and silver at an interface between laminated layers, thus completely avoiding the cause of discoloration.

(3) According to the present embodiment, silver is supported on an inorganic substance. This configuration prevents loss of a silver component over time and migration of a silver component to the polyvinyl chloride resin layer.

(4) According to the present embodiment, cross-linking of the surface protective layer 50 enables blocking of the migration of a silver component to the polyvinyl chloride resin layer.

(5) According to the present embodiment, the surface protective layer 50 is cross-linked by high energy such as ultraviolet light or an electron beam. This results in a higher degree of cross-linking, which further suppresses the migration of silver to the polyvinyl chloride resin layer.

(6) According to the present embodiment, with the following expression $D50 \leq Dsurf < 3 \times D50$ (1) holding, where D50 is the median diameter (µm) of silver-based additive particles 60 each comprising an inorganic substance and silver supported on the inorganic substance; and Dsurf is a coating amount (g/m²) defined as the density of the outermost layer of the surface protective layer 50 per square meter, parts of silver-supporting carriers protrude from the surface protective layer 50, which enhances antimicrobial and antiviral effects.

(7) According to the present embodiment, with the following expression $A \times B \times C \geq 10$ (2) holding, where A is the solid-content concentration (mass %) of the silver-based additive components in the outermost layer of the surface protective layer 50; B is the proportion (mass %) of silver in the silver-based additive particles 60; and C is the density (g) of the silver-based additive particles 60 per square meter of the outermost layer of the surface protective layer 50, the product of the component amount of the silver-based additive particles 60, the amount of silver supported in the silver-based additive particles 60, and the above density corresponds to the concentration of the active ingredient, and if this product is 10 or more, an antiviral activity value of 3 or more (reduction of viruses by 99.9%) is achieved.

A method according to the present embodiment for producing a decorative sheet includes:

laminating a pattern layer 30 on a surface of a printing substrate 20;

laminating a transparent polyvinyl chloride resin layer 40 on the surface of the pattern layer 30;

laminating a transparent surface protective layer 50 on the surface of the transparent polyvinyl chloride resin layer 40, the surface protective layer 50 being composed of an undercoat layer (e.g., the third surface protective layer 53) and a top coat layer (e.g., the first surface protective layer 51), the step of laminating the transparent surface protective layer 50 including:

a first step of applying, to the surface of the polyvinyl chloride resin layer 40, a first coat of resin free from silver components including silver (e.g., silver-based additive particles 60), and curing the first coat to form an undercoat layer (e.g., the third surface protective layer 53); and a second step of applying, to the surface of the undercoat layer (e.g., the third surface protective layer 53), a top coat of resin containing silver components (e.g., silver-based additive particles 60) while being free from chlorine-containing components, and then curing the top coat to cause cross-linking thereof, to thereby form a top coat layer (e.g., the first surface protective layer 51).

The above cross-linking enables blocking of the migration of a silver component to the polyvinyl chloride resin layer.

EXAMPLES

The present invention will be described in detail below by way of Examples 1 to 19 and Comparative Example 1. Note, however, that the present invention is not limited to the following Examples 1 to 19.

Example 1

In Example 1, using a 70-µm-thick colored sheet (comprised of polyvinyl chloride) as a printing substrate 20, vinyl chloride-vinyl acetate copolymer-based ink (cyan, magenta, yellow) was gravure printed on the surface of the printing substrate 20 to form a pattern layer 30.

Transparent polyvinyl chloride was laminated at a thickness of 100 µm on the surface of the pattern layer 30 using a thermal lamination method to form a polyvinyl chloride resin layer 40.

A surface protective layer 50 having three layers comprised of an acrylic material was formed by gravure coating on the surface of the polyvinyl chloride resin layer 40 to thereby produce a decorative sheet 10 of Example 1.

Table 1 below shows the composition of the surface protective layer 50.

TABLE 1

| | Undercoat | | | | | Top coat | | | | |
|---|---|---|---|---|---|---|---|---|---|---|
| | Base material | | Antiviral agent | | | Base material | | Antiviral agent | | |
| | Coating material | Material | Product | Content (on dry basis) | Density | Coating material | Material | Product | Content (on dry basis) | Density |
| Ex. 1 | UC Clear | Acrylic | PTC-NT ANV additive (ST) | 5 wt % | 3 g/m² | UC Clear | Acrylic | PTC-NT ANV additive (ST) | 5 wt % | 3 g/m² |
| Ex. 2 | UC Clear | Acrylic | None | None | None | UC Clear | Acrylic | " | " | " |
| Ex. 3 | UC Clear/Curing agent W325N = 100/10 | Acrylic + Isocyanate | " | " | " | UC Clear/Curing agent W325N = 100/10 | Acrylic + Isocyanate | " | " | " |
| Ex. 4 | UVT Clear | Acrylic | " | " | " | UVT Clear | Acrylic | " | " | " |
| Ex. 5 | EBT Clear | Acrylic | " | " | " | EBT Clear | Acrylic | " | " | " |
| Comp. Ex. 1 | SOLBIN CL | Vinyl chloride-vinyl acetate copolymer resin | PTC-NT ANV additive (ST) | 5 wt % | 3 g/m² | SOLBIN CL | Vinyl chloride-vinyl acetate copolymer resin | PTC-NT ANV additive (ST) | 5 wt % | 3 g/m² |
| Ref. Ex. | UC Clear | Acrylic | None | None | None | UC Clear | Acrylic | None | None | None |

That is, as shown in Table 1, the base material of the undercoat of the surface protective layer 50 was the coating material "UC Clear", which was acrylic. The antiviral agent of the undercoat was the product "PTC-NT ANV additive (ST)" such that the amount thereof contained in the undercoat (on a dry basis) was 5 wt %, and the density thereof was 3 g/m².

The base material of the top coat was the same as that of the undercoat. The antiviral agent of the top coat was the same as that of the undercoat.

Example 2

A decorative sheet of Example 2 was obtained under the same conditions as for Example 1, except that there was no antiviral agent in the undercoat.

Example 3

As shown in Table 1, a decorative sheet of Example 3 was obtained under the same conditions as for Example 1, except that the base material of the undercoat was the coating material "UC Clear, curing agent W325N=100/10", which was acrylic+isocyanate; no antiviral agent was used; and the base material of the top coat was the coating material "UC Clear, curing agent W325N=100/10", which was acrylic+isocyanate.

Example 4

As shown in Table 1, a decorative sheet of Example 4 was obtained under the same conditions as for Example 1, except that the base material of the undercoat was the coating material "UVT Clear", which was acrylic; no antiviral agent was used; and the base material of the top coat was the coating material "UVT Clear", which was acrylic.

Example 5

As shown in Table 1, a decorative sheet of Example 5 was obtained under the same conditions as for Example 1, except that the base material of the undercoat was the coating material "EBT Clear", which was acrylic; no antiviral agent was used; and the base material of the top coat was the coating material "EBT Clear", which was acrylic.

Example 6

Table 2 below shows the composition of the surface protective layer 50 of Example 6.

TABLE 2

| | Undercoat | | | | | Top coat | | | | |
|---|---|---|---|---|---|---|---|---|---|---|
| | Base material | | Antiviral agent | | | Base material | | Antiviral agent | | |
| | Coating material | Material | Product | Content (on dry basis) | Density | Coating material | Material | Product | Content (on dry basis) | Density |
| Ex. 3 | UC Clear/Curing agent W325N = 100/10 | Acrylic + Isocyanate | None | None | None | UC Clear/Curing agent W325N = 100/10 | Acrylic + Isocyanate | PTC-NT ANV additive (ST) | 5 wt % | 3 g/m² |
| Ex. 6 | " | " | " | " | " | " | " | " | 3 wt % | " |
| Ex. 7 | " | " | " | " | " | " | " | " | 2 wt % | " |

TABLE 2-continued

|  | Undercoat | | | | | Top coat | | | | |
| --- | --- | --- | --- | --- | --- | --- | --- | --- | --- | --- |
|  | Base material | | Antiviral agent | | | Base material | | Antiviral agent | | |
|  | Coating material | Material | Product | Content (on dry basis) | Density | Coating material | Material | Product | Content (on dry basis) | Density |
| Ex. 8 | " | " | " | " | " | " | " | " | 1 wt % | " |
| Ex. 9 | " | " | " | " | " | " | " | " | 5 wt % | 2 g/m² |
| Ex. 10 | " | " | " | " | " | " | " | " | 5 wt % | 1 g/m² |
| Ex. 11 | " | " | " | " | " | " | " | PTC-NT ANV additive (S1) | 5 wt % | 3 g/m² |
| Ex. 12 | " | " | " | " | " | " | " | " | 3 wt % | " |
| Ex. 13 | " | " | " | " | " | " | " | " | 2 wt % | " |
| Ex. 14 | " | " | " | " | " | " | " | " | 1 wt % | " |
| Ex. 15 | " | " | " | " | " | " | " | " | 5 wt % | 2 g/m² |
| Ex. 16 | " | " | " | " | " | " | " | " | 5 wt % | 1 g/m² |
| Ex. 17 | " | " | " | " | " | " | " | BIOSAIDO TB-B100 | 5 wt % | 3 g/m² |
| Ex. 18 | " | " | " | " | " | " | " | " | " | 2 g/m² |
| Ex. 19 | " | " | " | " | " | " | " | " | " | 1 g/m² |

That is, a decorative sheet of Example 6 was obtained under the same conditions as for Example 3, except that the amount of the antiviral agent contained in the top coat of the surface protective layer 50 (on a dry basis) was 3 wt % instead of 5 wt % in Example 3 as shown in Table 2.

Example 7

As shown in Table 2, a decorative sheet of Example 7 was obtained under the same conditions as for Example 3, except that the amount of the antiviral agent contained in the top coat (on a dry basis) was set to 2 wt %.

Example 8

As shown in Table 2, a decorative sheet of Example 8 was obtained under the same conditions as for Example 3, except that the amount of the antiviral agent contained in the top coat (on a dry basis) was set to 1 wt %.

Example 9

As shown in Table 2, a decorative sheet of Example 9 was obtained under the same conditions as for Example 3, except that the density of the antiviral agent in the top coat (on a dry basis) was set to 2 g/m².

Example 10

As shown in Table 2, a decorative sheet of Example 10 was obtained under the same conditions as for Example 3, except that the density of the antiviral agent in the top coat (on a dry basis) was set to 1 g/m².

Example 11

As shown in Table 2, a decorative sheet of Example 11 was obtained under the same conditions as for Example 3, except that the antiviral agent of the top coat was the product "PTC-NT ANV additive (S1)".

Example 12

As shown in Table 2, a decorative sheet of Example 12 was obtained under the same conditions as for Example 3, except that the antiviral agent of the top coat was the product "PTC-NT ANV additive (S1)", and that the amount thereof contained in the top coat (on a dry basis) was 3 wt %.

Example 13

As shown in Table 2, a decorative sheet of Example 13 was obtained under the same conditions as for Example 3, except that the antiviral agent of the top coat was the product "PTC-NT ANV additive (S1)", and that the amount thereof contained in the top coat (on a dry basis) was 2 wt %.

Example 14

As shown in Table 2, a decorative sheet of Example 14 was obtained under the same conditions as for Example 3, except that the antiviral agent of the top coat was the product "PTC-NT ANV additive (S1)", and that the amount thereof contained in the top coat (on a dry basis) was 1 wt %.

Example 15

As shown in Table 2, a decorative sheet of Example 15 was obtained under the same conditions as for Example 3, except that the antiviral agent of the top coat was the product "PTC-NT ANV additive (S1)", and that the density thereof in the top coat (on a dry basis) was 2 g/m².

Example 16

As shown in Table 2, a decorative sheet of Example 16 was obtained under the same conditions as for Example 3, except that the antiviral agent of the top coat was the product "PTC-NT ANV additive (S1)", and that the density thereof in the top coat (on a dry basis) was 1 g/m².

Example 17

As shown in Table 2, a decorative sheet of Example 17 was obtained under the same conditions as for Example 3, except that the antiviral agent of the top coat was the product BIOSAIDO TB-B100.

Example 18

As shown in Table 2, a decorative sheet of Example 18 was obtained under the same conditions as for Example 3, except that the antiviral agent of the top coat was the product BIOSAIDO TB-B100, and that the density thereof in the top coat was 2 g/m².

Example 19

As shown in Table 2, a decorative sheet of Example 19 was obtained under the same conditions as for Example 3, except that the antiviral agent of the top coat was the product BIOSAIDO TB-B100, and that the density thereof in the top coat was 1 g/m².

Comparative Example 1

As shown in Table 1, a decorative sheet of Comparative Example 1 was produced using the same method as that for Example 1, except that the base material of the undercoat and the top coat of the surface protective layer 50 was the coating material "SOLBIN CL" (available from Nissin Chemical Industry Co., Ltd.), which was a vinyl chloride-vinyl acetate copolymer resin.

Reference Example

As shown in Table 1, a decorative sheet of Reference Example was produced using the same method as that for Example 1, except that no antiviral agent was contained in the undercoat and the top coat of the surface protective layer 50.

[Evaluation Criterion 1]

The color difference ΔE (00) was measured between each of the produced decorative sheets of Examples 1 to 5 and Comparative Example 1 and the decorative sheet of Reference Example.

The color difference ΔE (00) was according to the method defined by the International Commission on Illumination (CIE) in 2000.

The decorative sheets of Examples 1 to 5, Comparative Example 1, and Reference Example were each heated in an oven at 80° C. for 10 days, followed by measurement of the color difference ΔE (2000).

[Evaluation Result 1]

The results are shown in Table 3.

TABLE 3

| | Color difference (difference relative to reference example) | |
|---|---|---|
| | Color difference | After 10 days of heating at 80° C. |
| Ex. 1 | 0.7 | 2.0 |
| Ex. 2 | 0.4 | 1.8 |
| Ex. 3 | 0.3 | 1.1 |
| Ex. 4 | 0.2 | 0.8 |
| Ex. 5 | 0.2 | 0.5 |
| Comp. Ex. 1 | >10 | >10 |

Compared with the Comparative Example, a color change after heating at 80° C. was small in the decorative sheets of Examples 1 to 5.

Here, a larger color difference indicates a greater color change (discoloration).

In Example 1, the undercoat of the surface protective layer 50 contained an antiviral agent, whereas in Examples 2 to 5, the undercoat of the surface protective layer 50 contained no antiviral agent. It can be inferred from this fact that the color difference was large in Example 1 due to the presence of an antiviral agent in the undercoat.

[Evaluation Criterion 2]

For the produced Examples 3 and 6 to 19, antiviral effects against influenza viruses were evaluated using a method according to ISO 21702.

The antiviral activity value was determined by the following expression (3):

$$V = (10 \times C \times D \times N)/A \quad (3)$$

V: Virus infectivity titer per square meter of sample (PFU/cm²)
C: Counted number of plaques
D: Dilution in well from which the counted number of plaques was obtained
N: Neutralizing solution amount
A: Area of contact between sample and viruses (area of polyethylene film)

[Evaluation Results 2]

Results are shown in Table 4.

TABLE 4

| | Dsurf | A × B × C | Antiviral activity value |
|---|---|---|---|
| Ex. 3 | 3 | 45 | >3.5 |
| Ex. 6 | 3 | 27 | >3.5 |
| Ex. 7 | 3 | 18 | >3.5 |
| Ex. 8 | 3 | 9 | 2.7 |
| Ex. 9 | 3 | 30 | >3.5 |
| Ex. 10 | 3 | 15 | >3.5 |
| Ex. 11 | 1 | 30 | 3 |
| Ex. 12 | 1 | 18 | 2.9 |
| Ex. 13 | 1 | 12 | 2.8 |
| Ex. 14 | 1 | 6 | 2.2 |
| Ex. 15 | 1 | 20 | >3.5 |
| Ex. 16 | 1 | 10 | 3 |
| Ex. 17 | 5 | 15 | >3.5 |
| Ex. 18 | 5 | 10 | 3.1 |
| Ex. 19 | 5 | 5 | 2.1 |

It was found that, for those Examples where the product (A×B×C) of the solid-content concentration A (mass %) of the silver-based additive components, the proportion B (mass %) of silver in the silver-based additive particles, and the density C (g) of the silver-based additive particles per square meter was 10 or more (A×B×C≥10), a particularly good antiviral activity value was obtained.

That is, in the case of the product (A×B×C) being 10 or more, an antiviral activity value of 3 or more (reduction of viruses by 99.9%) is achieved.

REFERENCE SIGNS LIST

10 . . . Decorative sheet; 20 . . . Printing substrate; 30 . . . Pattern layer; 40 . . . Polyvinyl chloride resin layer; 50 . . . Surface protective layer; 51 . . . First surface protective layer; 52 . . . Second surface protective layer; 53 . . . Third surface protective layer; 60 . . . Silver-based additive particles.

What is claimed is:
1. A decorative sheet comprising:
   (a) a base substrate consisting of polyvinyl chloride;
   (b) a pattern layer directly on the base substrate;
   (c) a polyvinyl chloride resin layer consisting of a polyvinyl chloride resin, the polyvinyl chloride resin layer being directly on the pattern layer;
   (d) a first surface protective layer consisting of acrylic material, the first surface protective layer being directly on the polyvinyl chloride resin layer;

(e) a second surface protective layer consisting of acrylic material, the second surface protective layer being directly on the first surface protective layer; and (f) a third surface protective layer consisting of acrylic material and silver-based additive particles, the third surface protective layer being the outermost layer of the decorative sheet and the third surface protective layer being directly on the second surface protective layer;

wherein the acrylic material of each of the first surface protective layer, the second surface protective layer and the third surface protective layer is selected from the group consisting of (a) acrylic resin and (b) a combination of acrylic resin and isocyanate; and wherein the acrylic material of the second surface protective layer is the same as the acrylic material of the third surface protective layer.

2. The decorative sheet of claim 1, wherein:
the acrylic material of the third surface protective layer has a cross-linked structure.

3. The decorative sheet of claim 2, wherein:
the cross-linked structure is formed by use of ultraviolet light.

4. The decorative sheet of claim 2, wherein:
the cross-linked structure is formed by use of an electron beam.

5. The decorative sheet of claim 1, wherein:
the following expression (1) is satisfied:

$$D50 \leq Dsurf < 3 \times D50 \qquad (1),$$

where: D50 is a median diameter (μm) of the silver-based additive particles; and
Dsurf is a coating amount (g/m$^2$) defined as a mass (g) of the third surface protective layer per square meter.

6. The decorative sheet of claim 1, wherein:
the following expression (2) is satisfied:

$$A \times B \times C \geq 10 \qquad (2),$$

where: A is a solid-content concentration (mass %) of the silver-based additive particles in the third surface protective layer;
B is a proportion (mass %) of silver in the silver-based additive particles; and
C is a mass (g) of the silver-based additive particles per square meter of the third surface protective layer.

7. The decorative sheet of claim 1, consisting of the base substrate, the pattern layer, the polyvinyl chloride resin layer, the first surface protective layer, the second surface protective layer, and the third surface protective layer.

8. The decorative sheet of claim 1, wherein each of the acrylic material of the second surface protective layer and the acrylic material of the third surface protective layer is acrylic resin.

9. The decorative sheet of claim 1, wherein each of the acrylic material of the second surface protective layer and the acrylic material of the third surface protective layer is a combination of acrylic resin and isocyanate.

10. A decorative sheet comprising:
(a) a base substrate consisting of polyvinyl chloride;
(b) a pattern layer directly on the base substrate;
(c) a polyvinyl chloride resin layer consisting of a polyvinyl chloride resin, the polyvinyl chloride resin layer being directly on the pattern layer;
(d) a first surface protective layer consisting of acrylic material, the first surface protective layer being directly on the polyvinyl chloride resin layer;
(e) a second surface protective layer consisting of acrylic material, the second surface protective layer being directly on the first surface protective layer; and
(f) a third surface protective layer consisting of acrylic material and silver-based additive particles, the third surface protective layer being the outermost layer of the decorative sheet and the third surface protective layer being directly on the second surface protective layer;

wherein the acrylic material of each of the first surface protective layer, the second surface protective layer and the third surface protective layer is selected from the group consisting of (a) acrylic resin and (b) a combination of acrylic resin and isocyanate;

wherein the acrylic material of the second surface protective layer is the same as the acrylic material of the third surface protective layer; and wherein the following expression (2) is satisfied:

$$A \times B \times C \geq 10 \qquad (2),$$

where: A is a solid-content concentration (mass %) of the silver-based additive particles in the third surface protective layer;
B is a proportion (mass %) of silver in the silver-based additive particles; and
C is a mass (g) of the silver-based additive particles per square meter of the third surface protective layer.

11. The decorative sheet of claim 10, wherein the following relationship is satisfied: $A \times B \times C \geq 15$.

12. The decorative sheet of claim 11, wherein the following relationship is satisfied: $Dsurf \geq 3$,
wherein Dsurf is a coating amount (g/m$^2$) defined as a mass (g) of the third surface protective layer per square meter.

13. The decorative sheet of claim 10, wherein each of the acrylic material of the second surface protective layer and the acrylic material of the third surface protective layer is acrylic resin.

14. The decorative sheet of claim 10, wherein each of the acrylic material of the second surface protective layer and the acrylic material of the third surface protective layer is a combination of acrylic resin and isocyanate.

* * * * *